(12) United States Patent
Gilboa

(10) Patent No.: US 7,876,942 B2
(45) Date of Patent: Jan. 25, 2011

(54) SYSTEM AND METHOD FOR OPTICAL POSITION MEASUREMENT AND GUIDANCE OF A RIGID OR SEMI-FLEXIBLE TOOL TO A TARGET

(75) Inventor: Pinhas Gilboa, Haifa (IL)

(73) Assignee: Activiews Ltd., Haifa (IL)

( * ) Notice: Subject to any disclaimer, the term of this patent is extended or adjusted under 35 U.S.C. 154(b) by 551 days.

(21) Appl. No.: 11/915,333

(22) PCT Filed: Mar. 29, 2007

(86) PCT No.: PCT/IL2007/000416

§ 371 (c)(1),
(2), (4) Date: Nov. 22, 2007

(87) PCT Pub. No.: WO2007/113815

PCT Pub. Date: Oct. 11, 2007

(65) Prior Publication Data

US 2008/0208041 A1      Aug. 28, 2008

Related U.S. Application Data

(60) Provisional application No. 60/787,149, filed on Mar. 30, 2006, provisional application No. 60/852,403, filed on Oct. 18, 2006, provisional application No. 60/887,605, filed on Feb. 1, 2007.

(51) Int. Cl.
*G06K 9/00*       (2006.01)
*A61B 5/05*       (2006.01)

(52) U.S. Cl. .................................. 382/128; 600/426

(58) Field of Classification Search ............... 382/128, 382/129, 130, 131, 132, 133, 134; 600/127, 600/129, 170, 171, 175, 176, 188, 222, 411, 600/427, 739, 426, 437, 443, 463; 604/14, 604/102.02, 166.01; 606/130
See application file for complete search history.

(56) References Cited

U.S. PATENT DOCUMENTS

| 6,216,029 B1 * | 4/2001 | Paltieli .................... 600/427 |
| 6,221,007 B1 * | 4/2001 | Green ....................... 600/160 |
| 2006/0094958 A1 * | 5/2006 | Marquart et al. ........... 600/434 |

* cited by examiner

*Primary Examiner*—Abolfazl Tabatabai
(74) *Attorney, Agent, or Firm*—Mark M. Friedman

(57) ABSTRACT

A system for measuring the position of a hand-held tool relative to a body in six degrees of freedom employs a camera attached via a mechanical linkage to the tool so that the camera moves together with the proximal portion of the tool and has a field of view including the distal end of the tool. A processing system processes images from the camera to determine a position of at least part of the tool. By employing optically identifiable fiducial reference points defined on the external surface of the body, a projection of the tool tip position onto a plane containing the target can be derived and displayed together with the target position, thereby facilitating guiding the tool to the target.

32 Claims, 10 Drawing Sheets

SYSTEM AND METHOD FOR OPTICAL POSITION MEASUREMENT AND GUIDANCE OF A RIGID OR SEMI-FLEXIBLE TOOL TO A TARGET

FIELD AND BACKGROUND OF THE INVENTION

The present invention relates to optical tracking systems and, in particular, it concerns a system and method for optical position measurement and guidance of a rigid or semi-flexible tool to a target.

Needle tools are often used in the medical field to deliver local treatment. In recent years, these procedures are carried by interventional radiologists, physicians who are experts in using imaging devices for guiding and controlling diagnostics and therapeutic procedures. In these procedures, the needles are inserted into the body under control of the imaging device.

Since the energy used by CT and fluoroscopy is X-ray, which is ionizing and harmful to living organs, image guided systems have been developed for navigating tools to a target based on preoperative CT data. Such navigation systems measure the location of the body and the location of the tool in six degrees of freedom and, by subtracting tool location from body location, determine the location of the tool relative to the body. At the beginning of the procedure, the CT data and the body are registered to match their coordinates. This is done by matching at least three fiducial points identified in the CT data and also in the body. In most such systems, one of two types of technology is used to determine the location of the tool and the body, that is: optical trackers and electromagnetic trackers. In optical trackers, the system makes use of two spaced apart video cameras and, by monitoring three or more identifiable light sources mounted on the tracked object, calculates the location and orientation of the object in up to six degrees of freedom (6 DOF) through triangulation calculations. In electromagnetic trackers, a transmitter having a plurality of antennae transmits a plurality of quasi-static magnetic fields. A receiver having a plurality of antennae receives these signals, and based on these signals calculates the location of the receiver relative the transmitter.

In these systems, the positions of both the tool and the body are determined relative to an intermediate reference system of coordinates, which is external to both the tool and the body. In the case of electromagnetic systems, the reference coordinates are defined by the transmitting antennae. In the optical trackers, the reference coordinates are defined by the camera. Subtracting the coordinates of the tool from that of the body yields the direct location of the tool in body coordinates. Since each position determination inherently adds some location error to the process, using an intermediate system of coordinate in determination of the position of the tool relative to the body is less accurate than could possibly be achieved by direct measurement of the position of the tool in body system of coordinates.

U.S. Pat. No. 6,216,029 to Paltieli describes free-hand directing of a needle towards a target located in a body volume. In this patent, the imaging device is a hand held ultrasound scanner. Electromagnetic location sensors are implemented in the transducer as well as in the handle of the tool. Both locations are determined relative to a reference coordinates frame defined by the electromagnetic tracking system.

The above described image guided systems are design to guide rigid tools to a target. However, needles, because of their small diameters tend to bend. Particularly when pushed percutaneously towards a target, the forces applied to manipulate and advance the needle often cause deflection. Since the location sensors in the aforementioned systems are attached to the proximal part of needle, measuring the orientation of the proximal portion without compensating for the deflection of the needle results in an erroneous location determination of the needle's distal tip. Consequently, the prediction of its path to the target will also be wrong.

Many of the internal organs of the body are covered by membranes such as pleura and peritoneum. These membranes are held in place by vacuum forces between the membrane and the outer organs. If the membrane is punctured, air leaks into the interspace between the membrane and the outer organ, causing the membrane to sink. In the lung this phenomenon is called Pneumothorax, and is very common, occurring in about 30% of the procedures of percutaneous thoracic needle biopsy.

There is therefore a need for a system and method for optical position measurement and guidance of a rigid or semi-flexible tool to a target which would measure the position of the tool directly in a set of coordinates fixed with the body. It would also be advantageous to provide a system and method for guiding a needle to a target including compensation for the deflection of the needle. Such a system would be expected to be highly advantageous for avoiding complications such as Pneumothorax.

SUMMARY OF THE INVENTION

The present invention is a system and method for optical position measurement and guidance of a rigid or semi-flexible tool to a target.

According to the teachings of the present invention there is provided, a system for measuring the position of a hand-held tool relative to a body in at least five degrees of freedom, the system comprising: (a) a rigid or semi-flexible tool having a distal end for insertion into the body, and a proximal portion for manual manipulation outside the body; (b) a camera for generating images; (c) a mechanical linkage attaching the camera to the tool such that: (i) the camera moves together with the proximal portion of the tool, and (ii) the camera is directed with a field of view including at least part of the distal end of the tool; and (d) a processing system in data communication with the camera and configured to process images from the camera to determine a position of at least part of the tool.

According to a further feature of the present invention, there is also provided a marker arrangement configured to be applied to an external surface of the body to provide a plurality of fiducial points, the processing system determining the position relative to the fiducial points.

According to a further feature of the present invention, the marker arrangement is implemented as a single patch carrying the plurality of fiducial points.

According to a further feature of the present invention, the plurality of fiducial points includes at least one set of four fiducial points, and wherein the patch is configured to maintain the set of four fiducial points substantially in a common plane.

According to a further feature of the present invention, the patch includes a plurality of markers configured to be readily detected by a non-optical imaging system.

According to a further feature of the present invention, the markers are coincident with the fiducial points on the patch.

According to a further feature of the present invention, the patch is configured to delineate a point of penetration of the distal end of the tool into the body.

According to a further feature of the present invention, the plurality of fiducial points include a first set of fiducial points and a second set of fiducial points optically distinguishable from the first set of fiducial points, the first set of fiducial points being more closely spaced than the second set of fiducial points.

According to a further feature of the present invention, the processing system is further configured to derive a current tip position of the distal end of the tool, the deriving including calculating an estimation of flexion of the tool, and employing the estimation of flexion to determine the current tip position.

According to a further feature of the present invention, the camera and at least part of the processing system are implemented on a common processor chip.

There is also provided according to the teachings of the present invention, a method for guiding a distal end of a rigid or semi-flexible tool to a target within a body, the tool having a proximal portion for manual manipulation from outside the body, the method comprising the steps of: (a) determining a spatial relation between a plurality of optically identifiable fiducial reference points defined on an external surface of the body and the target; (b) providing a camera mechanically attached to the proximal portion of the tool; and (c) during insertion of the tool into the body: (i) obtaining from the camera images of the external surface of the body including a plurality of the fiducial points, (ii) deriving from positions of the fiducial points in the images a current tip projection corresponding substantially to a point of intersection between an extrapolation from the distal end of the tool taken in a pointing direction of the distal end with a plane containing the target and substantially perpendicular to the pointing direction of the distal end of the tool, and (iii) displaying a graphic representation of at least the position of the target and the current tip projection.

According to a further feature of the present invention, the plurality of fiducial points on the external surface of the body are defined by applying to the external surface of the body a marker arrangement.

According to a further feature of the present invention, the marker arrangement is implemented as a single patch carrying the plurality of fiducial points.

According to a further feature of the present invention, the plurality of fiducial points includes at least one set of four fiducial points, and wherein the patch is configured to maintain the set of four fiducial points substantially in a common plane.

According to a further feature of the present invention, the spatial relation between the fiducial reference points and the target is determined using a non-optical imaging system, and wherein the patch includes a plurality of markers configured to be readily detected by the non-optical imaging system.

According to a further feature of the present invention, the markers are coincident with the fiducial points on the patch.

According to a further feature of the present invention, insertion of the tool into the body is performed through the patch.

According to a further feature of the present invention, the patch is configured to delineate a point of penetration of the distal end of the tool into the body.

According to a further feature of the present invention, a point of penetration of the distal end of the tool into the body is derived by processing of the camera images during performance of the method.

According to a further feature of the present invention, the plurality of fiducial points include a first set of fiducial points including a first optically distinct marking and a second set of fiducial points including a second optically distinct marking optically distinguishable from the first optically distinct marking, the first set of fiducial points being closer to the point of penetration than the second set of fiducial points.

According to a further feature of the present invention, the non-optical imaging system is a computerized tomography system.

According to a further feature of the present invention, the non-optical imaging system is a magnetic resonance imaging system.

According to a further feature of the present invention, the non-optical imaging system is a fluoroscope; the spatial relation between the fiducial reference points and the target being determined from images derived along at least two non-parallel viewing directions.

According to a further feature of the present invention, the tool has an elongated body with a direction of elongation, and wherein the camera is mechanically attached to the proximal portion of the tool so as to lie adjacent to the elongated body with a field of view including the direction of elongation.

According to a further feature of the present invention, prior to insertion of the tool into the body, a length calibration procedure is performed including: (a) touching the distal end of the tool against a reference point located in defined spatial relation to the fiducial points; (b) deriving the current camera position; and (c) deriving from the current camera position and from the position of the reference point a distance of the distal end from the camera.

According to a further feature of the present invention, a current tip position of the distal end of the tool is derived, the deriving including calculating, from a combination of the current camera position and a point of penetration of the tool into the body, an estimation of flexion of the tool, and employing the estimation of flexion to determine the current tip position.

According to a further feature of the present invention, the graphic representation is displayed as an overlay to the image obtained from the camera.

According to a further feature of the present invention, the graphic representation further includes a visual indication associated with each fiducial point indicative that the corresponding fiducial point in the image is being successfully tracked.

According to a further feature of the present invention, the graphic representation further includes an indication of a distance from the distal end to the target.

According to a further feature of the present invention, the graphic representation further includes a representation of the current tip position.

There is also provided according to the teachings of the present invention, a method for guiding a distal end of a semi-flexible tool to a target within a body, the tool having a proximal portion for manual manipulation from outside the body, the method comprising the steps of: (a) employing a position tracking system to monitor a current position of the proximal portion of the tool; (b) determining a location of penetration of the tool into the body; (c) deriving from the current position of the proximal portion of the tool and from the location of penetration an estimation of flexion of the tool, and hence a current tip position of the distal end of the tool within the body; and (d) displaying a graphic representation of at least: (i) the position of the target, and (ii) the intersection of an extrapolation from the distal end of the tool taken in a pointing direction of the distal end with a plane containing the target and substantially perpendicular to the pointing direction of the distal end.

There is also provided according to the teachings of the present invention, a patch for attachment to the skin of a body for use together with an optical guidance system for guiding a distal end of a rigid or semi-flexible tool to a target within a body, the tool having a proximal portion for manual manipulation from outside the body, the patch comprising: (a) a lower surface for adhering temporarily to the skin; (b) an upper surface provided with a set of at least four optically detectable fiducial points; (c) a plurality of contrast-generating features configured to provide high contrast points under operation of a non-optical imaging system for enabling localization of the patch using a non-optical imaging system; and (d) an insertion configuration configured to delineate a point of penetration of the distal end of the tool into the body.

According to a further feature of the present invention, the contrast-generating features are implemented as radio-opaque features.

According to a further feature of the present invention, the radio-opaque features are implemented as a radio-opaque substance added to a die employed to form the fiducial points.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a system and method for optical position measurement and guidance of a rigid or semi-flexible tool to a target.

The principles and operation of systems and methods according to the present invention may be better understood with reference to the drawings and the accompanying description.

Generally speaking, the present invention provides a system for measuring the position of a hand-held tool relative to a body in at least five degrees of freedom. The system operates with a rigid or semi-flexible tool having a distal end for insertion into the body, and a proximal portion for manual manipulation outside the body. A camera for generating images is attached via a mechanical linkage to the tool such that the camera moves together with the proximal portion of the tool, and that the camera is directed with a field of view including the distal end of the tool. A processing system in data communication with the camera and configured to process images from the camera to determine a position of at least part of the tool.

The present invention also provides a method for guiding a distal end of a rigid or semi-flexible tool to a target within a body. In general terms, the method includes determining a spatial relation between a plurality of optically identifiable fiducial reference points defined on the external surface of the body and the target. A camera, mechanically attached to the proximal portion of the tool, is then used during insertion of the tool into the body to obtain images of the external surface of the body including a plurality of the fiducial points. The images are then processed to derive from positions of the fiducial points a current tip projection corresponding substantially to a point of intersection between an extrapolation from the distal end of the tool taken in a pointing direction of the distal end with a plane containing the target and substantially perpendicular to the pointing direction of the distal end of the tool. A graphic representation is then displayed showing at least the position of the target, and the current tip projection, thereby facilitating guiding of the tool to the target.

At this stage, it will already be apparent that the system and method of the present invention offer profound advantages over the aforementioned prior art. Specifically, by mounting the camera directly on the tool, the use of an additional frame of reference external to both the tool and the body is avoided. This and other advantages of the present invention will become clearer from the subsequent detailed description.

Figure 1:
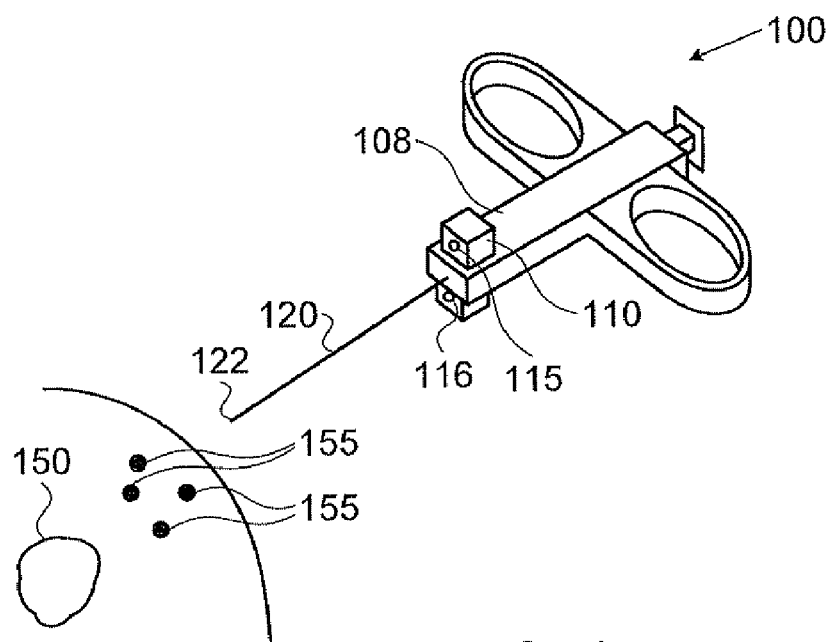
FIG. 1 is a schematic isometric representation illustrating the underlying principles of the system according to this invention.

Turning now to the drawings, the basic setup of the apparatus according to this invention is shown in FIG. 1. A handheld tool 100 has a proximal end 108 and a distal end 122. Its distal end is guided to target 150 for treatment to be performed by the tool at this target. A tracking module 110 is rigidly mounted on the proximal end of the tool, preferably on its handle. The tracking module denotes the location of the distal tip 122 of the tool 120, at least in position, preferably also in direction relative to target 150. Determination of the location of the tool relative to the body is performed directly between the tracking module and the body, without the need for an intermediate measurement between the tool and intermediate reference system. In a first preferred embodiment of tracking module 110, it includes a single camera 115. In a second preferred embodiment of the tracking module, it includes in addition, a second camera 116. These cameras are used for imaging and for identifying unambiguously a plurality of reference marks 155 which are part of, or adjacent in a fixed position to, target 150. Concurrently, the cameras are also image at least part of tool 120.

Preferably camera 115 and 116 are of an autonomic single-chip type, such as a CMOS camera, allowing the camera and at least part of the processing system to be implemented on a common processor chip. In this case, the chip preferably contains all of the necessary electronics to produce a video signal, typically including: a clock generator, timing generator, rows and column selectors and/or shift registers, output driver, exposure compensation mechanisms if required, gain and offset control if required and any other electronic circuitry needed to let this single-chip camera independently produce a video signal. The term video is used herein in its broader sense, to describe any type of camera output for delivering a stream of images including analog output, digital output, compressed digital output etc., and does not necessarily imply an output at a frame rate normally considered continuous video. Although the camera can be designed and manufactured in CCD technology supported by peripheral electronics, it is preferably made in CMOS technology because of its ability to combine logic and sensing cells in the same physical dye. The camera lens is preferably a single plastic molded lens.

Figure 2:
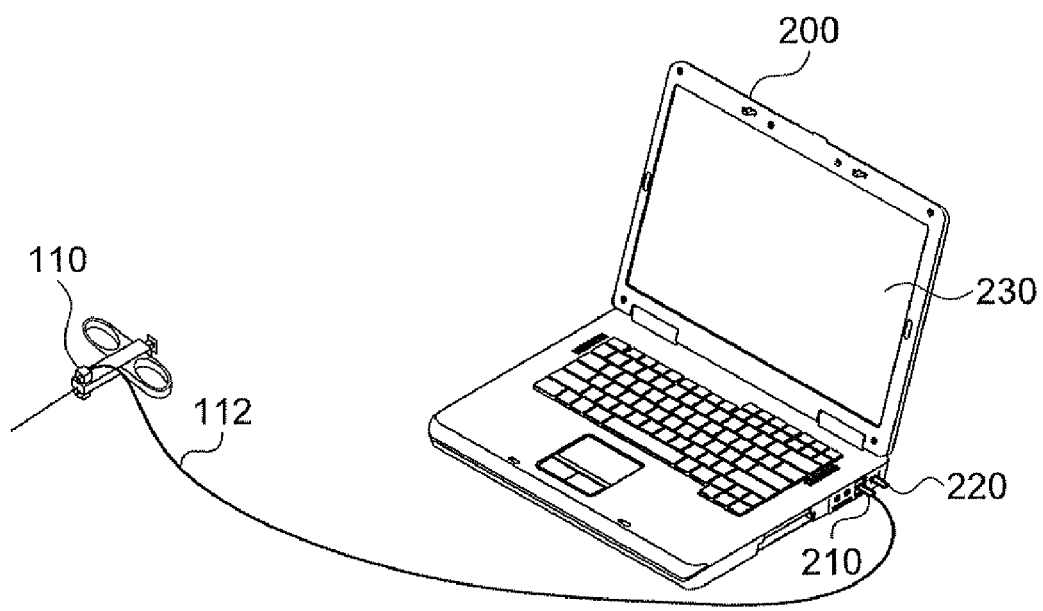
FIG. 2 is a schematic isometric representation of a preferred embodiment of a tracking system, constructed and operative according to the teachings of the present invention.

The preferred embodiment of the tracking apparatus is described schematically in FIG. 2. The video output signal of the cameras is fed to a frame grabber 210. The transfer of the video signal can be done through wire 112, but in one preferred embodiment of the invention it is accomplished wirelessly. The video signals digitized by the frame grabber 210 are fed to computer 200, which determines the position of the tracking module 110 relative to the tracked object, and determines guiding instructions that are displayed on display 230. In another preferred embodiment, the analog to digital converter is part of the camera, and the transfer of data to the computer is done digitally. The computer is preferably a notebook PC.

Figure 6:
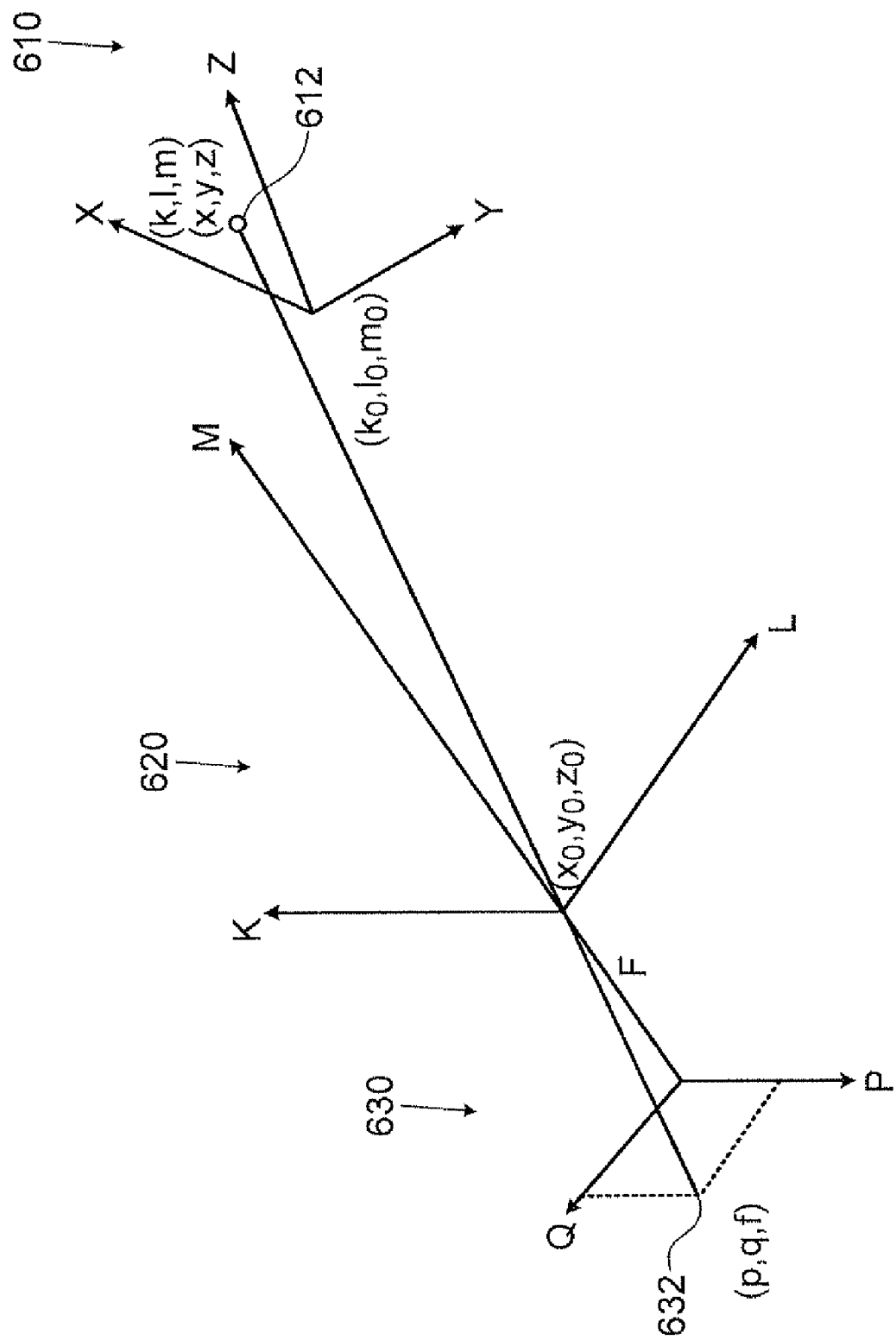
FIG. 6 is a schematic representation of a system of coordinates used in the description of a mathematical calculations employed in a preferred implementation of the present invention.
Figure 7A:
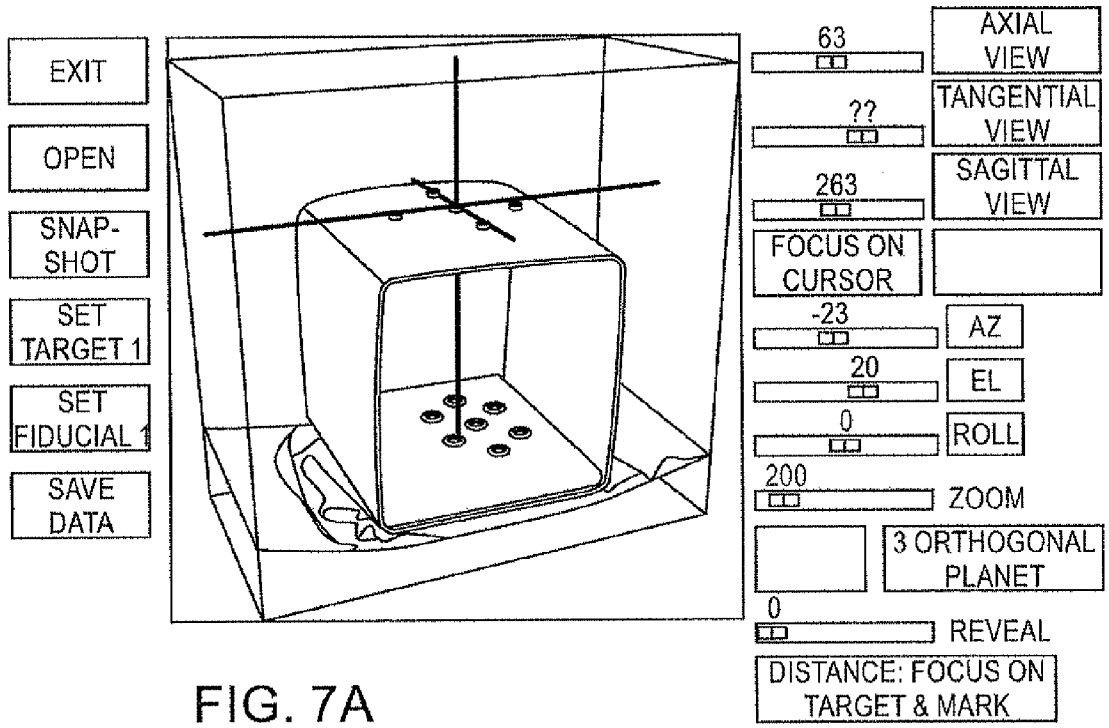
FIG. 7*a* and FIG. 7*b* are screen-shots exemplifying stages of a planning phase of a procedure illustrated using a plastic box as a sample object.
Figure 7B:
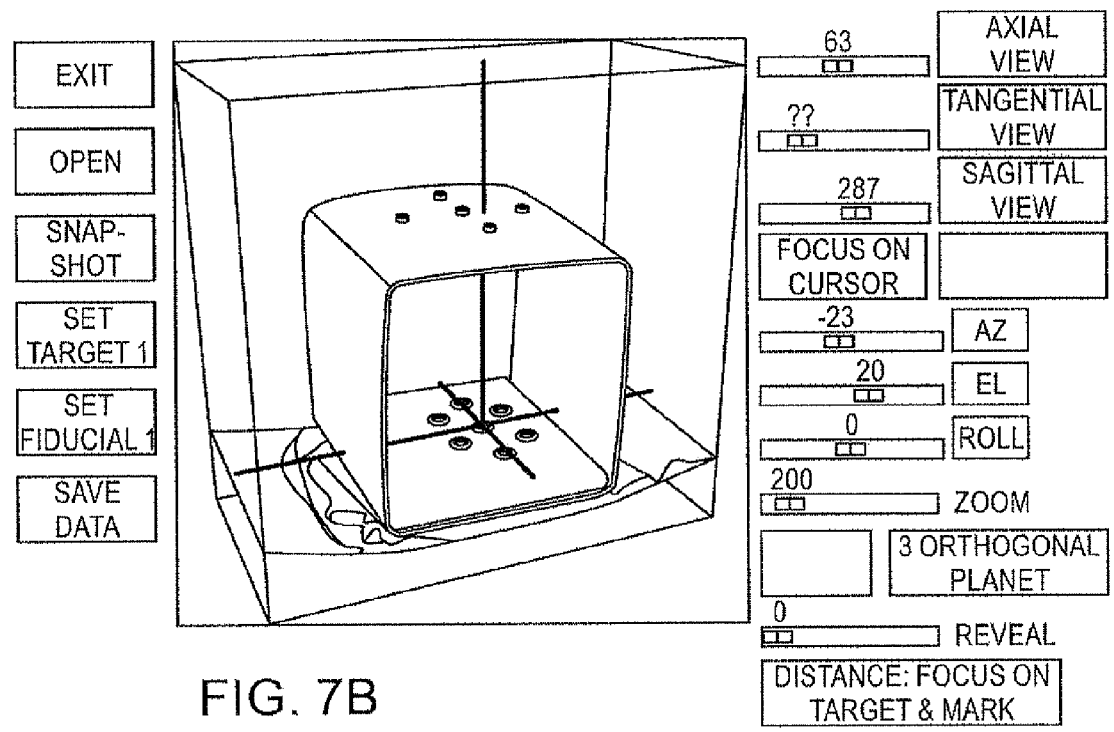

A system of coordinates, in the context of the mathematics employed in a preferred illustrative example of the present invention, is describes in FIG. 6. The tracked object defines a Cartesian system-of-coordinates 610. The object is viewed by a lens defining a system-of-coordinates 620. The lens is projecting an object point 612 to an image point 632 defined in an image system-of-coordinates 630. Point 612 is defined in a system-of-coordinates 610 by vector x=(x,y,z) and in system-of-coordinates 620 by vector $\underline{k}$=(k,l,m). The projection of this point on the image plane is the vector (p,q,f). We define the transformation from the object to the lens system-of-coordinates as the translation represented by vector $\underline{k_0}$=(k_0,l_0,m_0) and as rotation represented by 3×3 orthonormal matrix T. The transformation between the object and the lens system of coordinate is:

$$k = \begin{bmatrix} k \\ l \\ m \end{bmatrix} = (T \cdot x + k_0) = \begin{bmatrix} T_{11} & T_{12} & T_{13} \\ T_{21} & T_{22} & T_{23} \\ T_{31} & T_{32} & T_{33} \end{bmatrix} \cdot \begin{bmatrix} x \\ y \\ z \end{bmatrix} + \begin{bmatrix} k_0 \\ l_0 \\ m_0 \end{bmatrix} \quad (1)$$

The image of point 612 at the focal plane of the first camera is then:

$$\begin{bmatrix} p_a \\ q_a \\ f_a \end{bmatrix} = s_a \cdot k \quad (2)$$

where $f_a$ is the focal length of the lens of the first camera and $s_a$ is its magnification. If a second camera is implemented, placed at distance $D_k$ in the direction of axis k, the image of point 612 at the focal plane of the second camera lens is:

$$\begin{bmatrix} p_b \\ q_b \\ f_b \end{bmatrix} = (s_b/s_a) \cdot \begin{bmatrix} p_a \\ q_a \\ f_a \end{bmatrix} + s_b \cdot \begin{bmatrix} D_k \\ 0 \\ 0 \end{bmatrix} \quad (3)$$

where $f_b$ is the focal length of the first camera lens and $s_b$ is its magnification. Since T is an orthonormal matrix, the product of the dot multiplication of the rows (or the columns) of the matrix yields:

$$T_{m,1:3} \cdot T_{n,1:3} = 1 \text{ for } m=n \quad (4)$$

0 for m≠n

It is sufficient to determine only four elements of matrix T for solving the values of the rest of the matrix using question (4). Determining the six degrees of freedom (location and orientation) of the camera is carried out by using known reference mark points, measuring their corresponding image coordinates and solving the translation $k_0$ and the rotation T using questions (1) to (4). There is a total of 7 unknowns to be solved. If only a single camera is used, four reference markers 612, with their position in the object system-of-coordinates known, should be used. Four reference markers are sufficient since for each reference there are two linearly independent image data ($p_i$ and $q_i$), yielding 4×2=8 independent equations for the 7 unknowns. With an additional camera, there is a displacement between the two images of the reference markers resulting from the two different point of views. It is easy to show that for any of these references, these displacements occur in the direction of the displacement between the cameras. Hence, for each of the references there is only one additional linearly independent measured data, so three references, with a total of 3×3=9 linearly independent equations are sufficient to solve the set of equations.

The reference markers, providing what are referred to as "fiducial points", could be any identifiable features such as spots or curves visually identifiable by shape, color or texture. These reference markers could be landmarks of apparent parts of the object, or could be specially added objects like physical objects or imprints. Additional options include actively illuminated markers, which may be light sources or reflectors for reflecting light originating from a light source mounted near the camera(s) or elsewhere. The option of actively illuminated markers allows for signal encoding which may simplify analysis of the video. In the case of active light sources, each marker may be distinctively encoded to facilitate unambiguous identification of each marker.

Optionally, in order to avoid ambiguity between the different fiducial points, one or more of the fiducial points of each set may be made distinguishable from the others, such as by employing a different shape, pattern or color. Alternatively, an additional marking, such as an arrow or the like, may be provided to uniquely define the orientation of the set of fiducial points. In certain cases, it has been found sufficient to provide an indication to the user of which way the device should be held relative to the patch orientation, and to rely on the user not to rotate the system to an extent which might result in ambiguity in the image processing.

Most preferably, a marker arrangement is implemented as a single patch for attachment to the surface of the body which carries a plurality of fiducial points. In certain preferred embodiments, in order to simplify the mathematical analysis for calculating position, the patch is configured to maintain a set of four fiducial points substantially in a common plane. This effect may be achieved in a number of ways, for example, by employing a rigid patch, or by employing a patch with limited flexibility which tends to bend only in one of two primary directions at a time. It should be noted that the co-planarity of the reference points is not a requirement of the system and, where sufficient processing power is available, may be superfluous.

In one preferred embodiment of the invention, the location of the references are known in object coordinates by, for instance, calibration done prior to the navigation phase of the procedure. The calibration may be performed by using mechanical means or determined based on imaging data, such as CT data.

The identification of the references in the video output from the camera can be determined by image processing methods. Such methods are well known in art and it is therefore within the capabilities of one ordinarily skilled in the art to write the necessary software code which will run on computer 200 and determine the coordinates of the reference markers from the video.

Three dimensional (3D) scanners for image the interior of a body are well known. For instance X-ray fluoroscopy, computer tomography (CT) magnetic resonance imaging (MRI), position emission tomography (PET) and ultrasound. According to one preferred embodiment of the invention, a patch applied to the surface of the body to provide the optical fiducial points also provides a plurality of markers configured to be readily detected by a non-optical imaging system to facilitate registration of the patch position relative to the target. Typically, this requires the presence of suitably chosen material which generates features of high contrast in the particular imaging technology used. For instance, the markers used in CT scanner are preferably made of tiny spheres of lead. The spheres could be embedded in a flat plastic disk. Positioning of the spheres anywhere within the patch so that they are in known spatial relation to the optical fiducial points is sufficient to allow registration. Most preferably, the position of the markers for the non-optical imaging system coincide with the optical fiducial points so that the optical fiducial points are directly derived from the scanned data. For example, according to one preferred option, color marks are printed above the spheres, so the coordinates of said spheres could be determined in both the scanned data and the image of the camera. Alternatively, the markers could be implemented by printing an appropriate contrast agent dyes which are easily seen in the CT (or the MRI) image, using silk screen method. For example, addition of iodine to a dye is effective to render it readily visible in CT imaging. The coordinates of these markers are then used as fiducial points to register the orientation of the camera and the CT volume data, allowing directing the tool to a target determined in the CT data. The mathematics for registration of one system-of-coordinates to another through common fiducial points is well known in the art (See for example Medical Image Registration by Hajnal Hill and Hawkes, CRC Press, 2001).

Other techniques may be used as an alternative to 3D imaging techniques such as CT or MRI for determining the relative position of the fiducial points and the target. By way of one non-limiting example, two non-parallel views derived from a fluoroscope (itself a two-dimensional imaging device) to determine the relative positions of the target and markers in the patch. In each view, the position of the fluoroscope in six degrees of freedom is determined from the position of markers in the patch as visualized in the fluoroscope view, in a manner similar to the optical processing of the fiducial points, and the target position is marked. The intersection of the lines corresponding to the target position in two non-parallel views provides localization of the target relative to the patch.

One parameter employed in calculations of the tool tip location and direction is the point of penetration of the tool into the body. In principle, the point of penetration could be chosen by the user in an arbitrary location on the surface of the body within the camera field of view and this location could be determined by image processing from the images from camera 115. In practice, it is typically preferred to take advantage of the presence of the patch to determine the penetration point more easily and/or with higher accuracy than would otherwise be possible. Thus, insertion of the tool into the body is preferably performed through the patch. In one particularly preferred implementation, the patch itself is configured to delineate a point of penetration of the distal end of the tool into the body. This may be achieved by providing a preformed aperture through which the tool is to be inserted. In this manner, once the location of the markers within the patch are registered relative to the target, the position of the insertion point is immediately known. In alternative implementations, the point of penetration of the distal end of the tool into the body may be derived by processing of the camera images during the procedure itself. In this case, the patch may advantageously feature a geometrical pattern, such as a rectangular grid, which facilitates image-processing-based calculation of the penetration location. The penetration location may be determined by bringing the tip of the tool in contact with the location immediately prior to penetration, or may be determined or made more precise by calculations performed after penetration as the tool is advanced.

According to one particularly preferred methodology, at the beginning of the procedure, a coordinator sticker or other "patch" made of a block or layer of material that contains the fiducial markers is attached to skin of the patient above the target. A CT (or other volume imaging) scan is performed. Locations of the markers and the target are determined and fed to computer 200, for instance via disk-on-key memory 220. Based on this data, navigation of the tool towards the target can be determined.

Figure 3A:
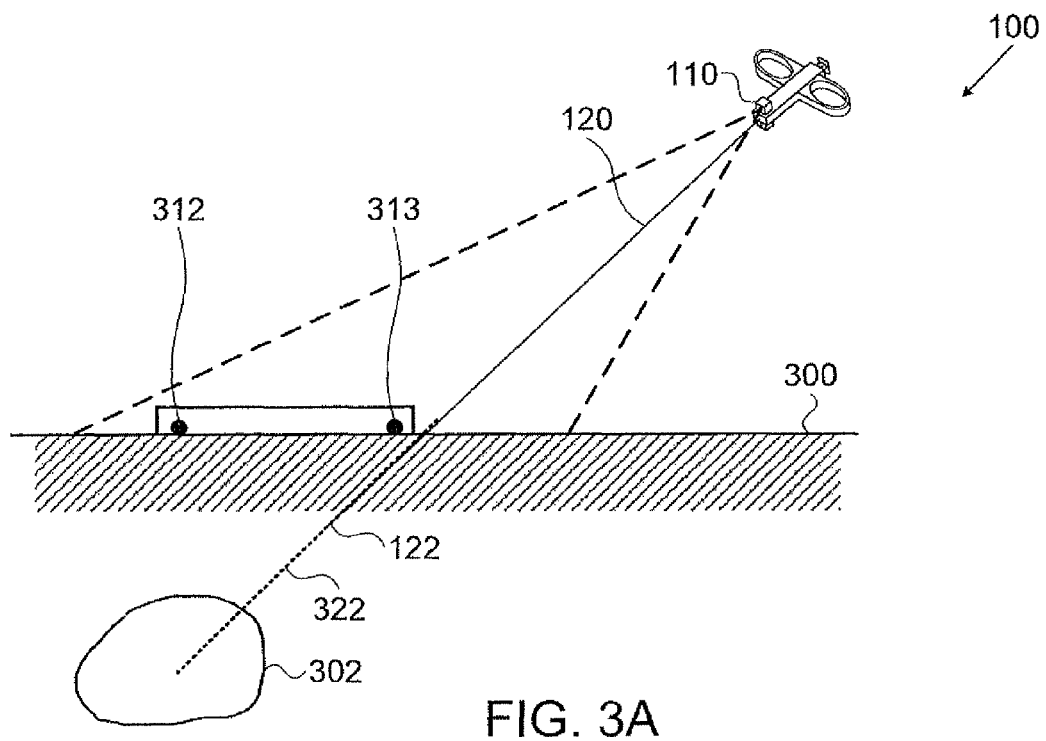
FIG. 3*a* and FIG. 3*b* are a schematic side view and corresponding camera image, respectively, illustrating a method of guiding a needle to a target in the absence of flexion of the needle.
Figure 3B:
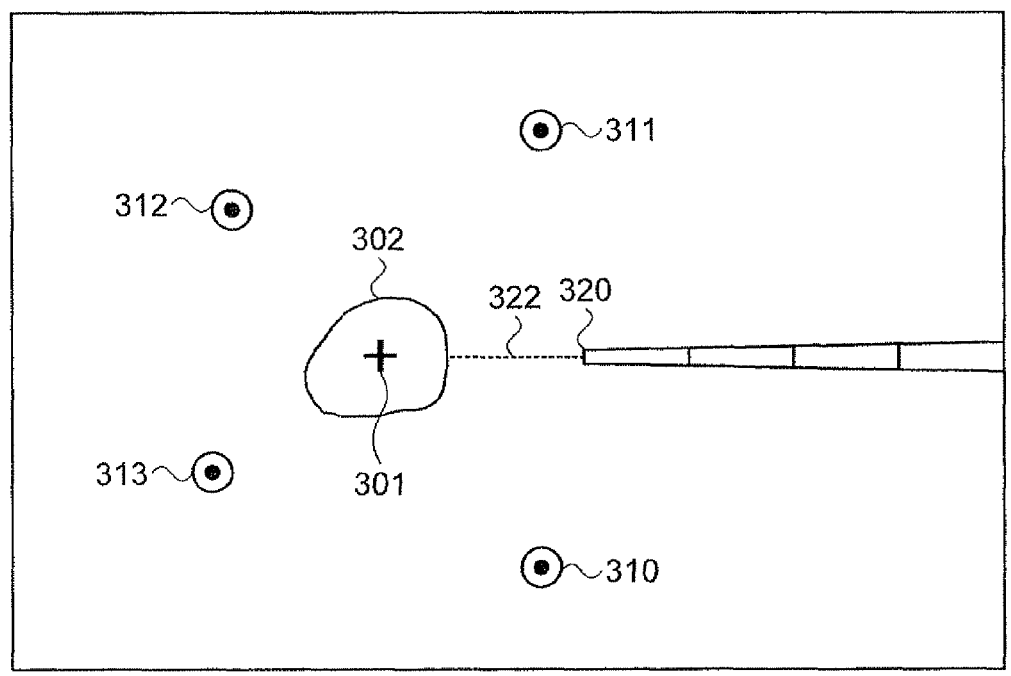
Figure 4A:
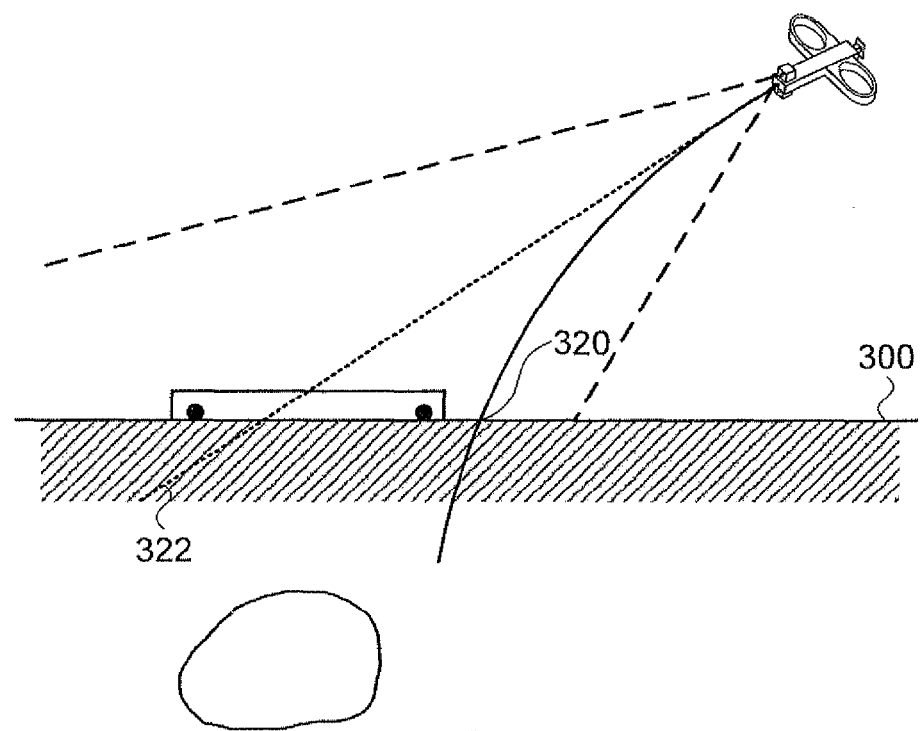
FIG. 4*a* and FIG. 4*b* are a schematic side view and corresponding camera image, respectively, illustrating errors arising from flexion of the needle.
Figure 4B:
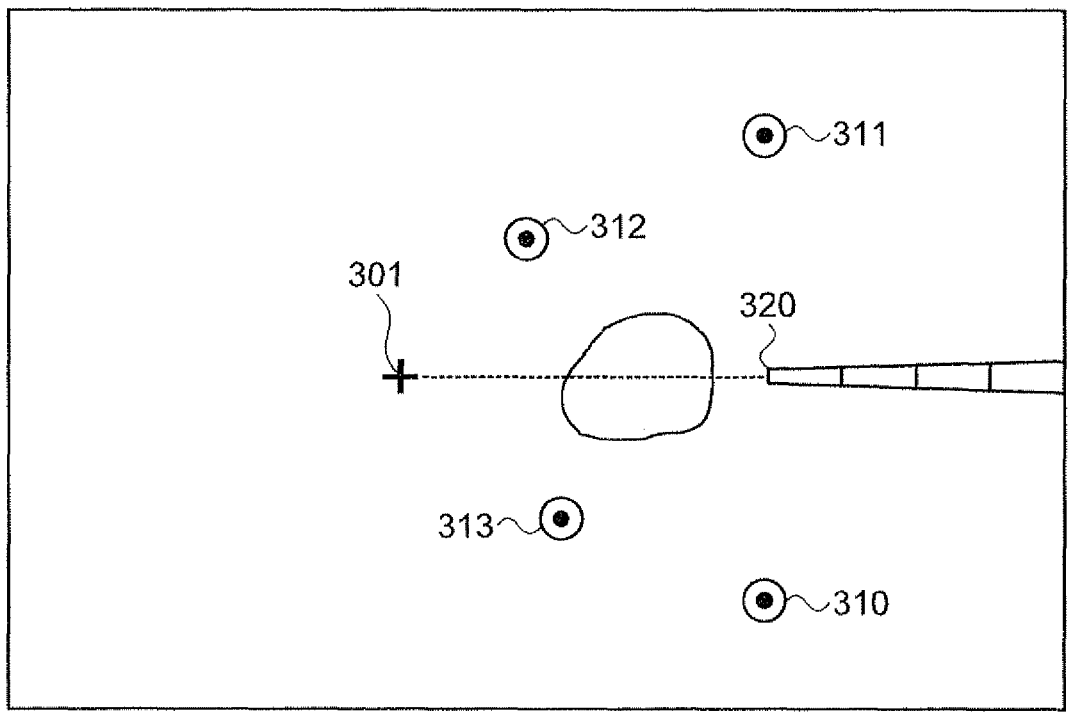

During navigation, compensation for the deflection of the tool should be introduced. In the description and claims, the terms "deflection", "flexion" and "bending" are used interchangeably to refer to temporary elastic deformation of the tool which introduces some degree of curvature relative to the unstressed state of the tool. The following example describes a preferred example of a method of compensation for a single camera tracking system. In FIGS. 3a and 3b, a scenario of a non-deflected tool is described. Camera module 110 is mounted on tool 100 at its proximal side, at a location and direction so that at least part of tool 120 is seen by the camera, together with the at least four markers, 310 to 313. Assumption is made here, that the geometry of the axis of the tool and its length in the camera system of coordinates are known in advance, either from design parameters or by calibration. Specifically with regard to the length of the tool, this may advantageously be determined at the beginning of the procedure by touching the distal tip of the tool against any point on the surface of the patch and actuating the system to determine the camera-to-patch distance. Since the patch itself is sterile, this does not present any problem in terms of operating procedures. Other calibration parameters are preferably pre-stored in the camera or provided on a data storage medium, as will be discussed below. The location and orientation of the imaging module 110 relative to the coordinator patch is determined. The location of the distal tip 122 of the tool can be determined by trajectory along its axis 322. The tip displayed above the image output from the camera, as shown by dash line 322 and by cross 301. Without deflection, the movements of the tip are the same as the movements of camera. When the tool is deflected, as shown in FIGS. 4a and 4b, without compensating for the deflection, errors are introduced. Since the trajectory of the tool is determined relative to the camera, and since the camera change its orientation with the deflection of the proximal end of the tool, the determined axis of the tool 322 no longer coincides with the actual axis of the distal part of the tool. As a result, the cross 301, representing the tip of the tool (or any other location along the direction of the needle such as the needle trajectory in the plane of the target), is displayed in an erroneous location on the display. If this situation is uncorrected, particularly for relatively flexible needles, it would often lead to unsuccessful navigation which would miss the intended target.

Figure 5A:
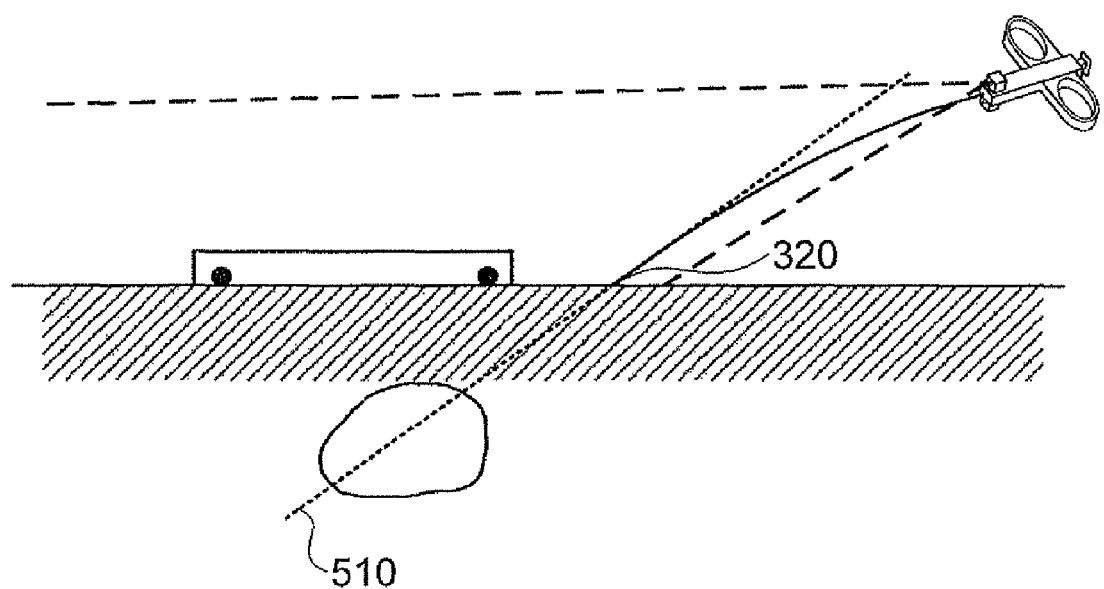
FIG. 5*a* and FIG. 5*b* are a schematic side view and corresponding camera image, respectively, similar to FIGS. 4*a* and 4*b*, illustrating compensation for errors due to flexion.
Figure 5B:
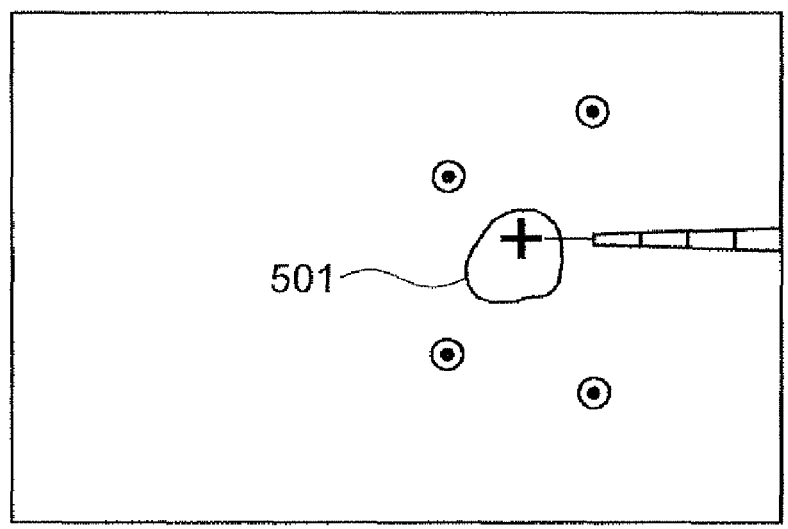

A number of models may be used to implement a correction for flexion of the tool. By way of one non-limiting example, corrections may be determined based on the assumption that point 320 where the tool enters the body lies in plane 300 of the coordinator patch. By solving equations (1) to (4), the location and orientation parameters of plane 300 are known. The path of the tool in the body, it's tip location and its intersection in the target plane are determined as the trajectory in the direction of said tangent direction, as shown in FIGS. 5a and 5b.

Figure 11:
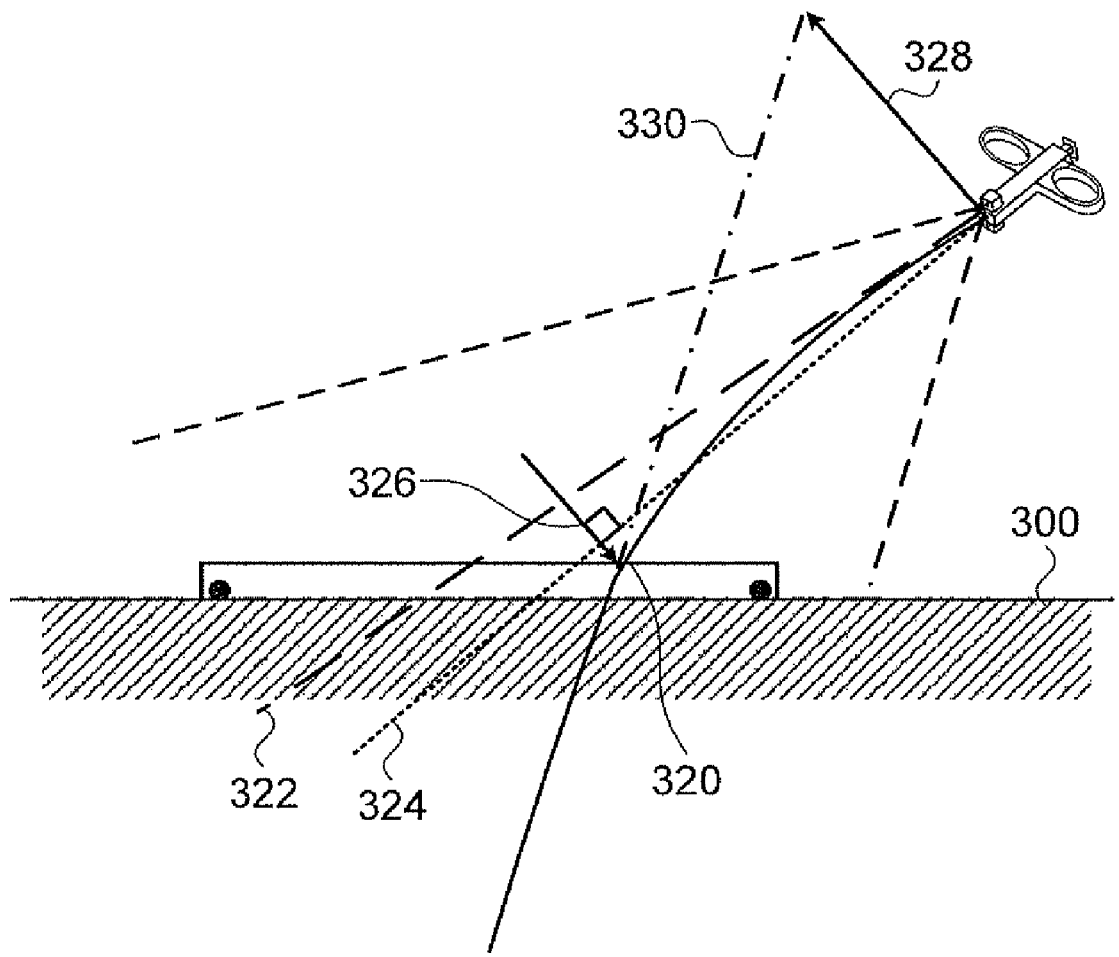
FIG. 11 is a schematic side view illustrating a preferred technique for correcting a pointing direction of a distal tip of a tool according to the teachings of the present invention.

It should be noted that various different models may be used to calculate the deflection of the tool based on any combination of the actual location of penetration, the theoretical non-deflected entry point, the length of the tool still outside the body and any other measured parameters, and hence to derive the pointing direction of the distal tip. In practice, a particularly simple calculation for the corrected pointing direction of the distal tip has been found highly effective for a wide range of implementations. This calculation will now be described with reference to FIG. 11.

Specifically, in the case illustrated here, the tool penetrates into the body at a known position 320 within the area of the patch. The theoretical unflexed path of the tool is represented by dashed line 322 while the optical axis of the camera is represented by dashed line 324. These axes are typically roughly parallel, and are defined by calibration data supplied with the system. A deflection vector 326 is defined as the vector from unflexed tool path 322 to point of penetration 320 which lies in a plane perpendicular to optical axis 324. In order to calculate a corrected direction of the tool within the body, a corrected theoretical tool position by correcting the current tool handle position by a correction vector 328 corresponding to a scaled value of the deflection vector 326 in an opposite direction. The scaling factor may be a constant, or may be a variable parameter such as, for example, a function of the length of the tool outside the body. The estimated pointing direction of the tool tip is then taken to be the line 330 passing from the corrected theoretical tool position through the actual point of insertion.

Typically, a constant scaling factor for correction vector 328 in the range between 1 and 3 has found to be effective. It has been found that it is not normally critical that the correction be a full correction. In fact, in certain cases, attempts to provide a full correction for the deflection may result in overcompensation by the user and/or scaling-up of any position measurement errors. In various practical implementations, highly effective results have been obtained using a scaling factor of about 1.5.

Compensation for deflection of the tool in a tracking system comprising two cameras is very similar, with the simplification that the arc of the deflected tool could be determined directly from the stereo-pairs images and determining the location of several points along the tool using equation (3).

In another preferred embodiment of the invention, the coordinator patch is implemented as a sticker made of a flexible material, of which one side is covered with adhesive to be stuck on the skin of the patient. The flexible material, preferably a polymer such as nylon or polyvinyl chloride (PVC), has tiny reference markers embedded in it. As before, these markers are preferably implemented using materials which provide high contrast under the non-optical imaging technique to be used for registration. In the case of the CT, these markers are radio-opaque, for instance made of tiny spheres of lead, typically with a diameter of one to two millimeters. In addition, optical fiducial points, such as "imprints", are printed on the surface of the sticker. These imprints could be lines, circles or any other shapes or optically distinctive features. They could be printed in single-color, or more preferably in multi-color for easier differentiation by color segmentation. Collectively, the imprints define a system-of-coordinates used for navigating the tool to the target. The embedded markers are used to register the location of the tool to the CT volume. The imprints are arranged such as to let the location of the embedded marks be determined from the images of the camera.

The size of area seen by optics of the tracking device is a function of its field-of-view (FOV) and the distance of the sticker from the lens. As the distance between the camera and the sticker is increases, so does the area covered by the optics. To maintain the accuracy of the system, it is preferred to have the fiducial points spaced apart as much as possible. During insertion of the tool into the body, the camera comes closer and closer to the sticker, so that its FOV covers a smaller and smaller area of it. Most preferably, in order to optimize the distribution of the fiducial points for both the initial positioning and the final stages of penetration, two or more sets of fiducial points, designated by optically distinct sets of features, are deployed at different spacings, one set more closely spaced so as to cover a smaller area and the other further apart and so as to be spread over a larger area.

According to an additional optional feature, certain locations on the patch may be designated as control locations associated with specific system functions. The system then monitors whether the system operator has brought the tip of the tool into contact (or close proximity) with one of the control locations and, if so, performs the corresponding allocated system function. Examples of system control functions which may be allocated to locations on the patch in this manner include, but are not limited to: initiating tool length recalibration, changing display modes or other parameters of the display, inputting any other real-time data or changing any other operational parameter of the system, and power-off. The use of touching the tool against a location on the patch as a user interface input is particularly advantageous in the context of the present invention since it avoids the need for the system operator to touch any non-sterile computer equipment or distract his or her attention from the vicinity in which the procedure is to be performed.

The system may be used to direct any thin long tool, such as a needle, a pointer etc. The tool may be rigid or semi-flexible. In this context, the term "rigid" is used to refer to tools which do not undergo flexion under normal conditions of use to a degree which significantly impacts precision of guidance of the tool to a target. In this context, the phrase "semi-flexible" is used to refer to tools which, under normal conditions of use, undergo deflection without major change of shape. Numerically, the term "semi-flexible" may be taken to refer to any elongated tool which in normal use remains with a flexion-induced curvature of radius greater than twice the length of the tool, and typically at least three times the length of the tool.

In one embodiment of the invention, the geometry of the tool is known in advance. In another embodiment, its geometry is determined during the procedure from the images. Although in the embodiment described above, the distal portion of the tool is partly hidden, this invention is also applicable in applications where the distal portion is seen in the entire operation. In such embodiment, the location of the distal tip of the tool is optionally determined directly from the video image.

In one preferred embodiment of the invention, the images are displayed on the computer screen. In another embodiment of the invention, goggles are used to allow three dimensional display which gives depth perception. In some embodiments, based on the location and angles of the tool relative to the body, virtual 3D images of the body can be produced from the 3D scanned data and display on the computer display, to show the path of the tool inside the interior body organs.

As mentioned earlier, the content of the display preferably includes a representation of the target position and a current tip projection along the pointing direction of the distal end projected onto a plane containing the target and substantially perpendicular to the pointing direction. The plane used for the projection may actually be a plane containing the target and perpendicular to the optical axis of the camera, but since deflections are typically relatively small, both such planes of projection are considered within the scope of the terminology "substantially perpendicular to the pointing direction".

In addition to the target position and current tip projection, various other items are preferably shown in the display to facilitate navigation of the tool to the target. According to a first particularly preferred option, the graphic representation of the target position and current tip projection is displayed as an overlay to the image obtained from the camera. This has been found very useful for helping the user to maintain his or her spatial orientation. Optionally, a visual indication may be displayed in association with each fiducial point indicative that the corresponding fiducial point in the image is being successfully tracked. Other items which may optionally be displayed include an indication of a distance from the distal end to the target, such as a numerical distance in millimeters, and a representation of the current tip position.

Figure 8:
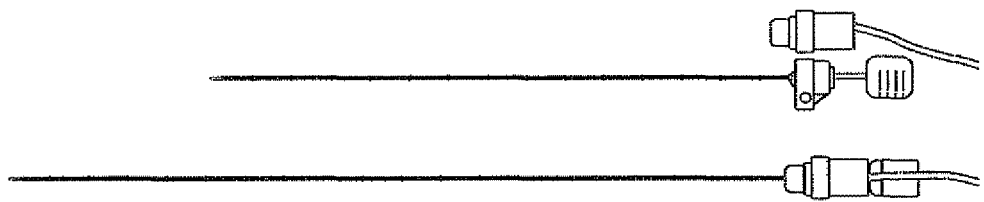
FIG. 8 is a side view of two needles equipped with a miniature camera according to the present invention.
Figure 9A:
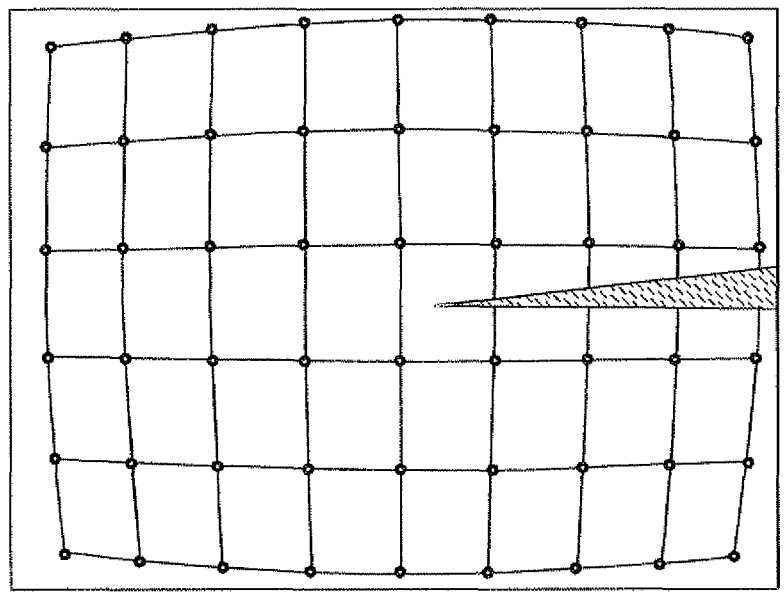
FIG. 9*a* and FIG. 9*b* are sample images from a miniature camera of the present invention showing an uncorrected, distorted view and a corrected version of the same view, respectively.
Figure 9B:
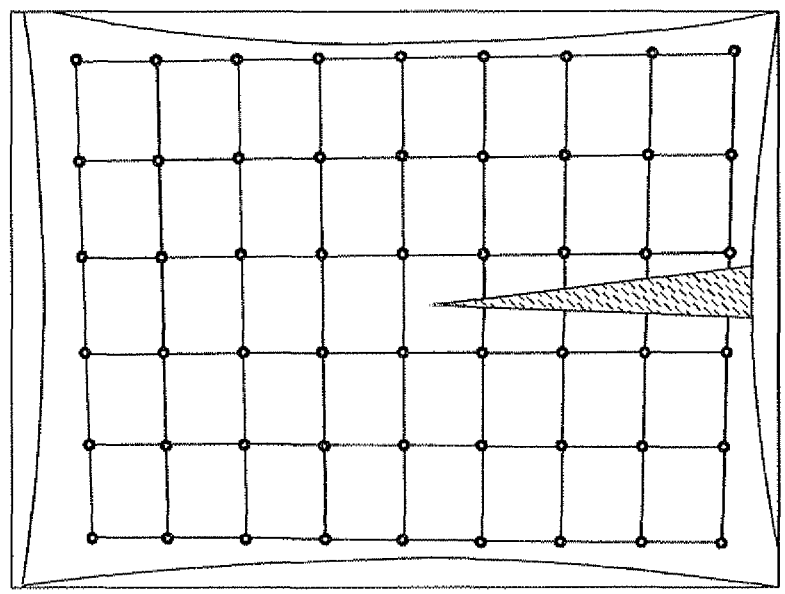

An example to the process of navigating a needle to a selected target is shown in FIGS. 7 to 10. An empty plastic box is used as a body, where targets are glued to its bottom and a coordinator sticker is stuck to its cover. First, the body (the box) is scanned by a CT scanner. The scanned data is fed to a computer program. Using that program, the positions of the fiducial points (FIG. 7a) and of the targets (FIG. 7b) are marked. A miniature camera is attached with the help of simple adaptor to a needle, as the examples in FIG. 8 are demonstrated. Often, the lens of the camera in used is distorting the image, as seen in FIG. 9a, and needs to be corrected, as shown in FIG. 9b. FIGS. 10a to 10d show the navigation screens of the system. Information is displayed above the original image 1300 of the camera. Coordinator sticker 1330 includes eight printed markers, four green markers 1310 and four blue markers 1314. The use of primary colors facilitates the identification of the markers during image processing and, at least for medical applications, red is preferably not used to avoid confusion due to the presence of blood in the field of view. As mentioned earlier, other types of optically distinctive markings may be used. The blue markers are more closely spaced within the larger region spanned by the green markers. Needle shaft 1120 is shown entering through the coordinator sticker at a predefined hole 1320. In FIG. 10a, the needle is not flexed, hence its axis 1322 coincides with the shaft 1120 of the needle. Target 1302 is presented by two colored concentric disks, a blue outer ring calibrated to display a disk of diameter of 10 mm, as measured in the target plan and an inner green disk, of disk of diameter of 5 mm, both centered at the target. The distance between the tip of the needle and the target is also displayed in a text box 1332.

Figure 10A:
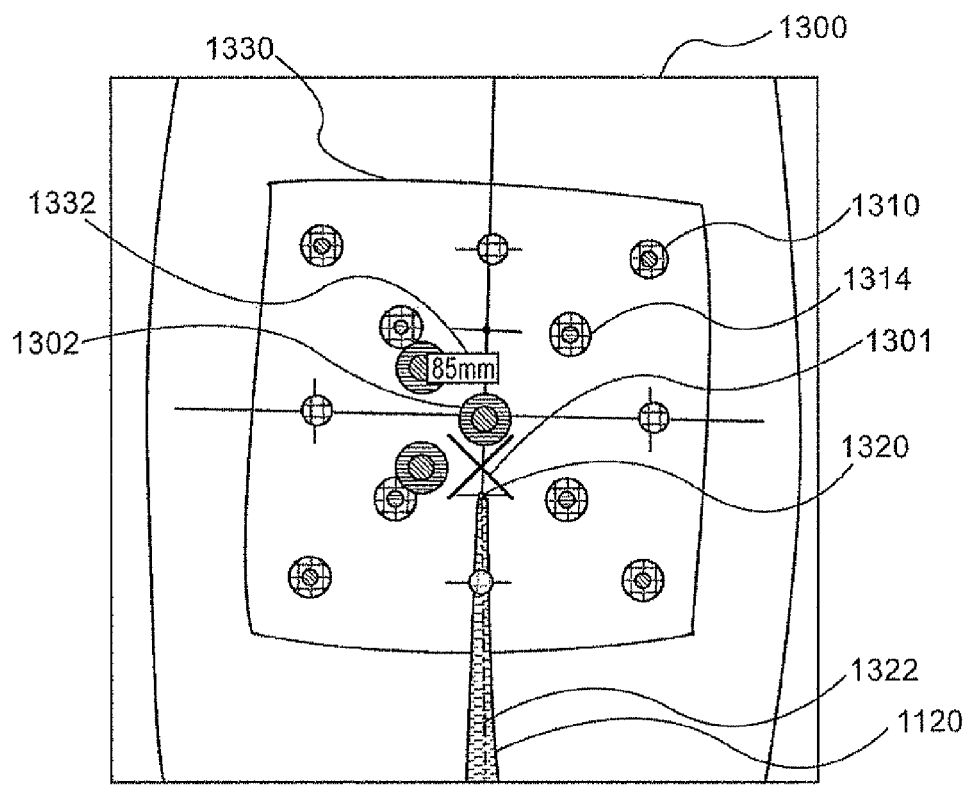
FIGS. 10*a* through 10*d* show a display of the present invention at different stages during performance of an exemplary procedure performed on the sample object of FIGS. 7*a* and 7*b*.
Figure 10B:
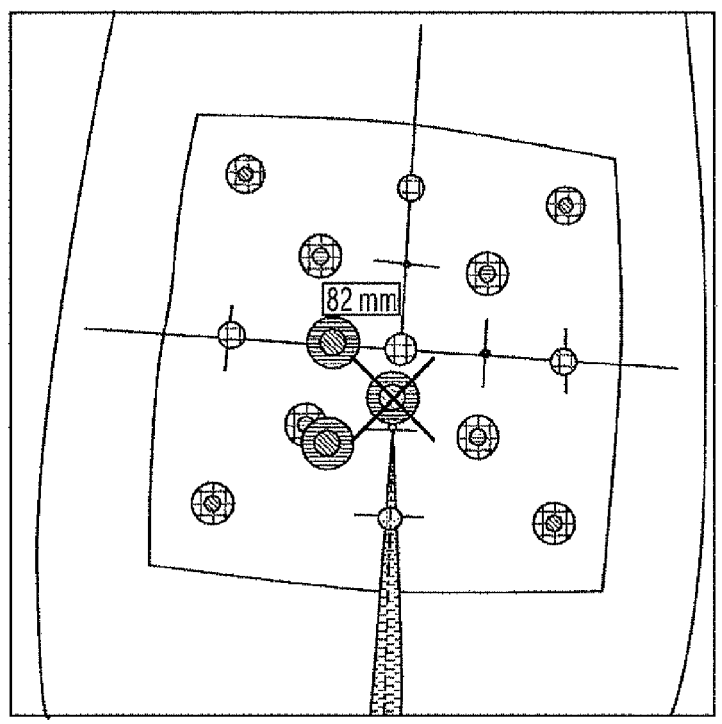
Figure 10C:
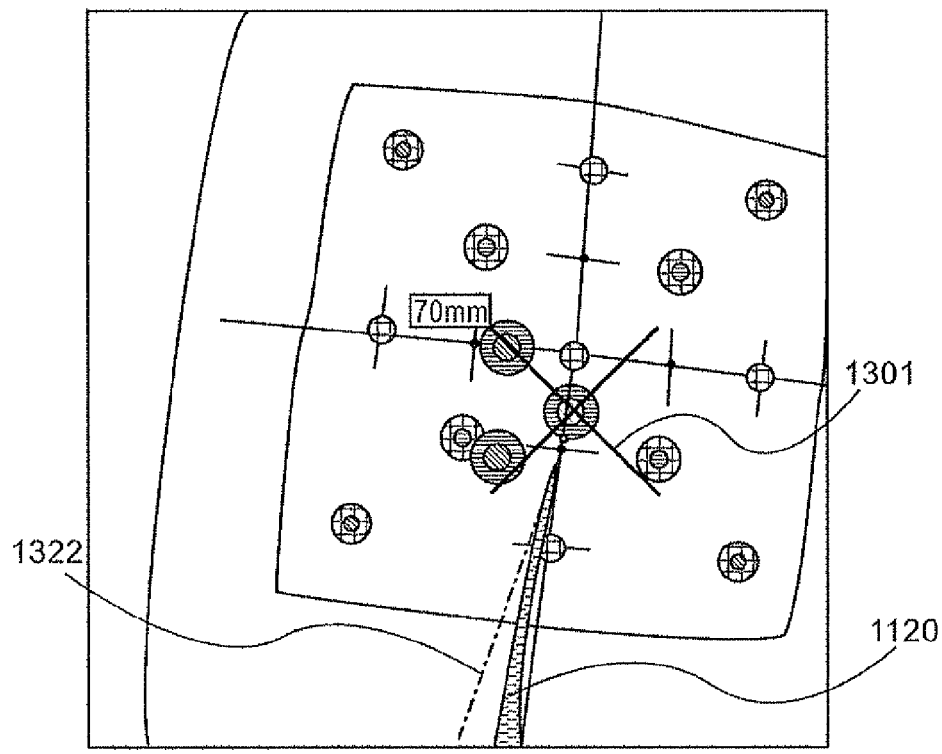
Figure 10D:
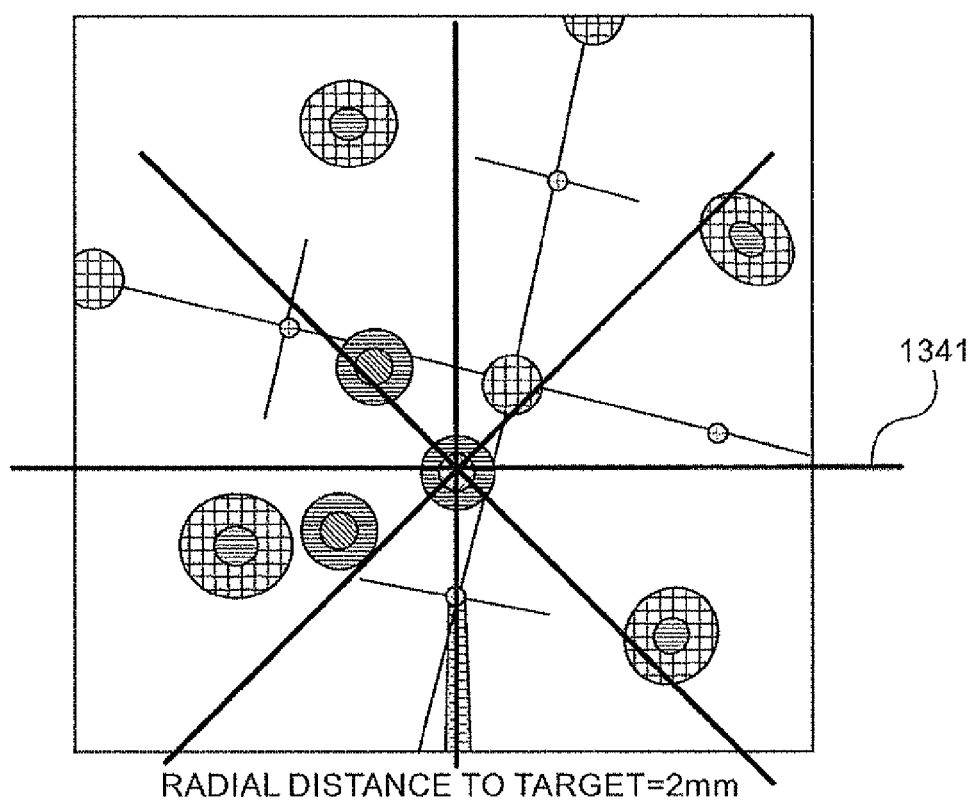

Aiming the needle at one of the targets, as shown in FIG. 10b, automatically selects this target, as indicated by the change of the green color to yellow. During guidance, the system determines the deflection of the needle's shaft. FIG. 10c shows the case where shaft 1120 is deflected. Because of that deflection, the predicted path of the needle 1322 (shown in dashed line) does not coincide with the image of the shaft. The cross reticle 1301 is preferably displayed in a distance-dependent size, thereby giving a sense of depth; as the tip-to-target distance decreases, the size of the reticle increases (and vice versa). Pushing the needle into the body reduces the distance between the camera and the coordinator sticker which reduce the area of the sticker covered by the field of view. In consequence, as is seen in FIG. 10d, the green markers disappeared outside of the camera view, leaving only the blue markers to guide the tool. When the tip of the needle reaches to the plane of target, the cross changes to a star shape reticle (1341 in FIG. 10d), to warn that no further advancing is required.

In estimating the deflection of the needle, other tracking technologies than the above described optical tracker may be used as well, typically with a similar conceptual approach based upon calculating the difference between the actual entry-point and the theoretically non-deflected entry-point. Such technologies include, but are not limited to, embedding a location sensor at the proximal end of the tool and another location sensor adjacent to the actual entry point of the tool into the body. Another method is to predict the deflection outside of the body by scanning coordinates marked along the needle shaft outside of the body and predicting therefrom the path inside the body. Such a scanning process may be performed by a scanner such as an optical stereoscopic scanner.

In predicting the path of the needle inside the body, the CT data may be used to evaluate some tissue mechanical parameters such as its flexibility and density along the predicted path and use it to predict the deflection of the needle.

Recently, CT fluoroscopy for interventional procedures was developed. In these scanners, an image of a single slice is produce continuously, allowing it to be used similar to real-time X-ray fluoroscopy imaging devices. The system of this invention has several advantages over CT fluoroscopy in guiding the tool to target. First, it allow continuous navigation of the tool in real-time without using the hazardous X-ray radiation. In addition, it allows navigating the tool in any direction, also perpendicular to the CT slices, in contrary to the use of the CT fluoroscopy which forces the practitioner to make the entire path in a single CT slice.

This system and method allows navigating the tool from any required side of the body of the patient, and is independent of orientation, even allowing navigation from beneath the body upwards, should that be considered advantageous for any particular procedure.

The distortion of the lens of the camera is preferably corrected by polynomials, as is known in the art. Each lens has its individual distortion which should be corrected individually. In a preferred embodiment of the invention, these polynomials are stored in a memory which is assembled as part of the camera, or supplied separated on a data storage medium supplied with the camera. These corrections preferably also include calibration corrections for any variation in the alignment of the camera relative to the tool due to manufacturing tolerances of the attachment bracket or the like. When the camera is connected to the system, the polynomials are read and fed to the algorithm, where the image from the camera is corrected individually by those polynomials.

It will be appreciated that the above descriptions are intended only to serve as examples, and that many other embodiments are possible within the scope of the present invention as defined in the appended claims.

What is claimed is:

1. A system for measuring the position of a hand-held tool relative to a body in at least five degrees of freedom, the system comprising:
   (a) a rigid or semi-flexible tool having a distal end for insertion into the body, and a proximal portion for manual manipulation outside the body;
   (b) a marker arrangement comprising a patch configured to be applied to an external surface of the body at a point of insertion of the tool into the body, said patch carrying a plurality of fiducial points;
   (c) a camera for generating images;
   (d) a mechanical linkage mounting said camera on said proximal portion of said tool such that:
      (i) said camera moves together with said proximal portion of said tool, and
      (ii) said camera is directed with a field of view including at least part of said patch when said patch is deployed on an external surface of the body and said distal portion of said tool in inserted into the body; and
   (e) a processing system in data communication with said camera and configured to process images from said camera to determine a position of at least part of said tool relative to said fiducial points.

2. The system of claim 1, wherein said plurality of fiducial points includes at least one set of four fiducial points, and wherein said patch is configured to maintain said set of four fiducial points substantially in a common plane.

3. The system of claim 1, wherein said patch includes a plurality of markers configured to be readily detected by a non-optical imaging system.

4. The system of claim 3, wherein said markers are coincident with said fiducial points on said patch.

5. The system of claim 1, wherein said patch is configured to delineate a point of penetration of the distal end of the tool into the body.

6. The system of claim 5, wherein said plurality of fiducial points include a first set of fiducial points and a second set of fiducial points optically distinguishable from said first set of fiducial points, said first set of fiducial points being more closely spaced than said second set of fiducial points.

7. The system of claim 1, wherein said processing system is further configured to derive a current tip position of the distal end of the tool, said deriving including calculating an estimation of flexion of the tool, and employing said estimation of flexion to determine said current tip position.

8. The system of claim 1, wherein said camera and at least part of said processing system are implemented on a common processor chip.

9. A method for guiding a distal end of a rigid or semi-flexible tool to a target within a body, the tool having a proximal portion for manual manipulation from outside the body, the method comprising the steps of:
   (a) determining a spatial relation between a plurality of optically identifiable fiducial reference points defined on an external surface of the body and the target;
   (b) providing a camera mechanically attached to the proximal portion of the tool; and
   (c) during insertion of the tool into the body:
      (i) obtaining from the camera images of the external surface of the body including a plurality of said fiducial points,
      (ii) deriving from positions of said fiducial points in said images a current tip projection corresponding substantially to a point of intersection between an extrapolation from the distal end of the tool taken in a pointing direction of the distal end with a plane containing the target and substantially perpendicular to the pointing direction of the distal end of the tool, and
      (iii) displaying a graphic representation of at least the position of the target and the current tip projection.

10. The method of claim 9, wherein said plurality of fiducial points on the external surface of the body are defined by applying to the external surface of the body a marker arrangement.

11. The method of claim 10, wherein said marker arrangement is implemented as a single patch carrying said plurality of fiducial points.

12. The method of claim 11, wherein said plurality of fiducial points includes at least one set of four fiducial points, and wherein said patch is configured to maintain said set of four fiducial points substantially in a common plane.

13. The method of claim 11, wherein said spatial relation between said fiducial reference points and the target is determined using a non-optical imaging system, and wherein said patch includes a plurality of markers configured to be readily detected by said non-optical imaging system.

14. The method of claim 13, wherein markers are coincident with said fiducial points on said patch.

15. The method of claim 11, wherein insertion of the tool into the body is performed through said patch.

16. The method of claim 15, wherein said patch is configured to delineate a point of penetration of the distal end of the tool into the body.

17. The method of claim 15, wherein a point of penetration of the distal end of the tool into the body is derived by processing of said camera images during performance of the method.

18. The method of claim 15, wherein said plurality of fiducial points include a first set of fiducial points including a first optically distinct marking and a second set of fiducial points including a second optically distinct marking optically distinguishable from said first optically distinct marking, said first set of fiducial points being closer to said point of penetration than said second set of fiducial points.

19. The method of claim 9, wherein the non-optical imaging system is a computerized tomography system.

20. The method of claim 9, wherein the non-optical imaging system is a magnetic resonance imaging system.

21. The method of claim 9, wherein the non-optical imaging system is a fluoroscope, the spatial relation between said fiducial reference points and the target being determined from images derived along at least two non-parallel viewing directions.

22. The method of claim 9, wherein the tool has an elongated body with a direction of elongation, and wherein said camera is mechanically attached to the proximal portion of the tool so as to lie adjacent to the elongated body with a field of view including the direction of elongation.

23. The method of claim 9, further comprising, prior to insertion of the tool into the body, performing a length calibration procedure including:

(a) touching said distal end of the tool against a reference point located in defined spatial relation to said fiducial points;
(b) deriving the current camera position; and
(c) deriving from said current camera position and from the position of said reference point a distance of said distal end from the camera.

24. The method of claim 9, further comprising deriving a current tip position of the distal end of the tool, said deriving including calculating, from a combination of said current camera position and a point of penetration of the tool into the body, an estimation of flexion of the tool, and employing said estimation of flexion to determine said current tip position.

25. The method of claim 9, wherein said graphic representation is displayed as an overlay to the image obtained from the camera.

26. The method of claim 25, wherein said graphic representation further includes a visual indication associated with each fiducial point indicative that the corresponding fiducial point in the image is being successfully tracked.

27. The method of claim 9, wherein said graphic representation further includes an indication of a distance from the distal end to the target.

28. The method of claim 9, wherein said graphic representation further includes a representation of the current tip position.

29. A method for guiding a distal end of a semi-flexible tool to a target within a body, the tool having a proximal portion for manual manipulation from outside the body, the method comprising the steps of:
(a) employing a position tracking system to monitor a current position of the proximal portion of the tool;
(b) determining a location of penetration of the tool into the body;
(c) deriving from said current position of the proximal portion of the tool and from said location of penetration an estimation of flexion of the tool, and hence a current tip position of the distal end of the tool within the body; and
(d) displaying a graphic representation of at least:
(i) the position of the target, and)
(ii) the intersection of an extrapolation from the distal end of the tool taken in a pointing direction of the distal end with a plane containing the target and substantially perpendicular to the pointing direction of the distal end.

30. A patch for attachment to the skin of a body for use together with an optical guidance system for guiding a distal end of a rigid or semi-flexible tool to a target within a body, the tool having a proximal portion for manual manipulation from outside the body, the patch comprising:
(a) a lower surface for adhering temporarily to the skin;
(b) an upper surface provided with a set of at least four optically detectable fiducial points;
(c) a plurality of contrast-generating features configured to provide high contrast points under operation of a non-optical imaging system for enabling localization of the patch using a non-optical imaging system; and
(d) an insertion configuration configured to delineate a point of penetration of the distal end of the tool into the body.

31. The patch of claim 30, wherein said contrast-generating features are implemented as radio-opaque features.

32. The patch of claim 31, wherein said radio-opaque features are implemented as a radio-opaque substance added to a die employed to form said fiducial points.

\* \* \* \* \*